(12) United States Patent
Rath

(10) Patent No.: US 7,056,950 B2
(45) Date of Patent: Jun. 6, 2006

(54) COMPOSITIONS OF BIOCHEMICAL COMPOUNDS INVOLVED IN BIOENERGY METABOLISM OF CELLS

(76) Inventor: Matthias Rath, Twenteport Oost 3, NL-7609 RG Almelo (NL)

( * ) Notice: Subject to any disclaimer, the term of this patent is extended or adjusted under 35 U.S.C. 154(b) by 57 days.

(21) Appl. No.: 10/077,283

(22) Filed: Feb. 14, 2002

(65) Prior Publication Data

US 2002/0173546 A1 Nov. 21, 2002

Related U.S. Application Data

(60) Provisional application No. 60/268,825, filed on Feb. 14, 2001.

(51) Int. Cl.
*A61K 31/00* (2006.01)

(52) U.S. Cl. .................. 514/553; 514/557; 514/566; 514/561; 514/683

(58) Field of Classification Search ................ 424/442, 424/439, 441, 438; 426/2; 514/175, 553, 514/566, 561, 683, 559, 557, 558
See application file for complete search history.

(56) References Cited

U.S. PATENT DOCUMENTS

| 4,981,687 | A | | 1/1991 | Fregly et al. |
|---|---|---|---|---|
| 5,328,701 | A | | 7/1994 | Richmond et al. |
| 5,378,722 | A | | 1/1995 | Madsen et al. |
| 5,904,924 | A | | 5/1999 | Gaynor et al. |
| 6,033,689 | A | * | 3/2000 | Waterman et al. .......... 426/2 |

FOREIGN PATENT DOCUMENTS

| DE | 39 43 424 A1 | 7/1991 |
|---|---|---|
| EP | 0 146 742 A1 | 7/1985 |
| EP | 0 617 958 A1 | 10/1994 |
| EP | 0 747 035 A2 | 12/1996 |
| GB | 2 322 551 A | 9/1998 |
| JP | 10333335 | 10/1998 |
| WO | 93/23027 | 11/1993 |
| WO | 94/1458 | 7/1994 |
| WO | 95/12991 | 5/1995 |
| WO | 95/15147 | 6/1995 |
| WO | 96/40167 | 12/1996 |
| WO | 97/09975 | 3/1997 |
| WO | 99/21565 | 5/1999 |
| WO | 02/058488 A2 | 8/2002 |
| WO | 02/058488 A3 | 8/2002 |

OTHER PUBLICATIONS http://www.health-pages.com/cs/.*
http://www.mothernature.com/shop/detail.cfm/sku/42778.*
The Merck Index, 12th edition, pp. 270-273 and 969.*
Sigma Catalog, 1994, pp. 772 and 950.*
http://www.wholehealthproducts.com/wholehealthproducts/index.cfm.*
http://www.mothernature.com/index.cfm.*
Bourgeron T., et al., *J. Clin. Invest.* 93:2514, 1994.
Rustin et al., *Biochim Biophys Acta* 1361:185, 1997.
Patel, M.S. and Harris R.A. *FASEB* 9:1164, 1995.
Shoffner, J.M. and Wallace D.C. in C.R. Scriver et al. (Eds.) *Tghe Metabolic and Molecular Bases of Inherited Disease*, 7th ed. New York: McGraw Hill, 1995, p. 1535.
Beyond deficiency, 2nd *Symposium of the New York Academy of Sciences on Vitamins*, New York 1992.
E.Ziegler, L.J. Filer (eds.) *Present Knowledge in Nutrition* 7th edition. ILSI Press, WashingtonD.C. 1996 (Chapters 15, 16, 17, 19, and 25).
Matthias Rath, Alexandra Niedzwiecki, *J Appl. Nutrition* 48: 68-78, 1996.
Stumpf et al., Friedreich attaxia: III. Mitochondrial Malic Enzym Deficiency, Neurology 1982; 32: 221-7.
Walker et al., *Journal of Inherited Metabolism Disorder* 12 (1989), 331-332.
Gellera et al., *Neurology* 1990, 40 (3 pt 1): 495-9.
Narajanan et al., *Journal of Children Neurologie* May 1996; 11 (3): 252-55.
Coughlin et al., *Mol. Genet. Meta.* Apr. 1998; 254-62.
*J. Med. Genet.* May 1995; 32 (5): 344-7).
*Neuropediatric* Feb. 2000; 31 (1): 35-8).

* cited by examiner

*Primary Examiner*—Irene Marx
(74) *Attorney, Agent, or Firm*—Kenyon & Kenyon LLP; Ali Kamarei, Esq.

(57) ABSTRACT

A composition of biochemical compounds involved in bioenergy metabolism of cells and a method of use in prevention and therapy of diseases are disclosed.

3 Claims, 3 Drawing Sheets

FIG. 1 is a graph showing the metabolic pathway of the Krebs cycle, also known as Tricarboxylic Acid Cycle or Citric Acid Cycle.
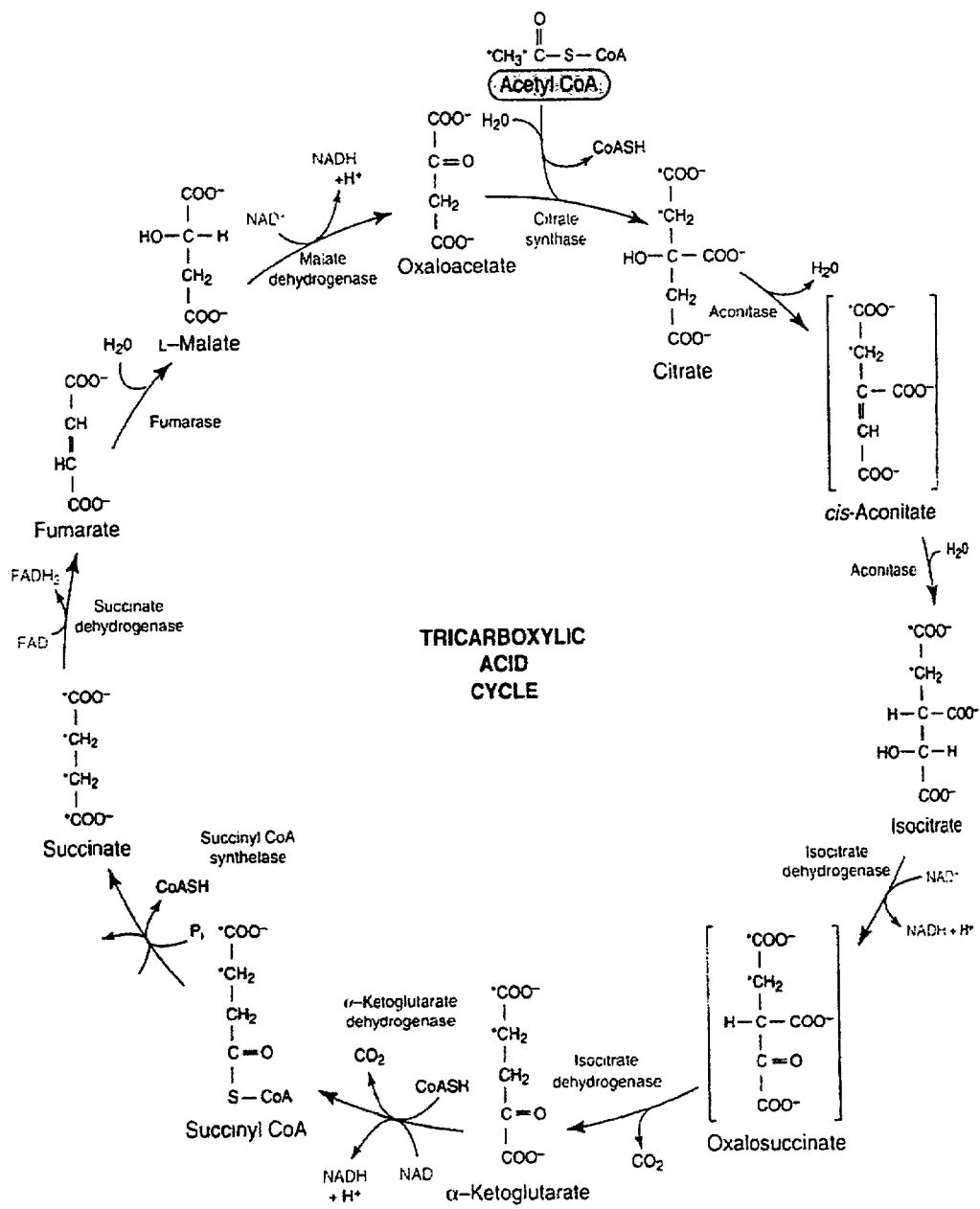

FIG. 2 shows the enzyme complex and prosthetic group involved in the metabolic pathway of Respiratory Chain, also known as Oxidative Phosphorylation.

|  | Enzyme Complex | Prosthetic Group |
|---|---|---|
| 5 | NADH-Q Reductase | Flavin Mononuceotide |
|  |  | Fe-S |
|  | Succinate-Q Reductase | FAD |
| 10 |  | Fe-S |
|  | Cytochrome Reductase | Heme b |
|  |  | Heme b |
|  |  | Heme c |
| 15 |  | Fe-S |
|  | Cytochrome c | Heme c |
|  | Cytochrome Oxidase | Heme a |
| 20 |  | Heme a |

FIG. 3 is a graph showing the metabolic pathway of Urea Cycle.
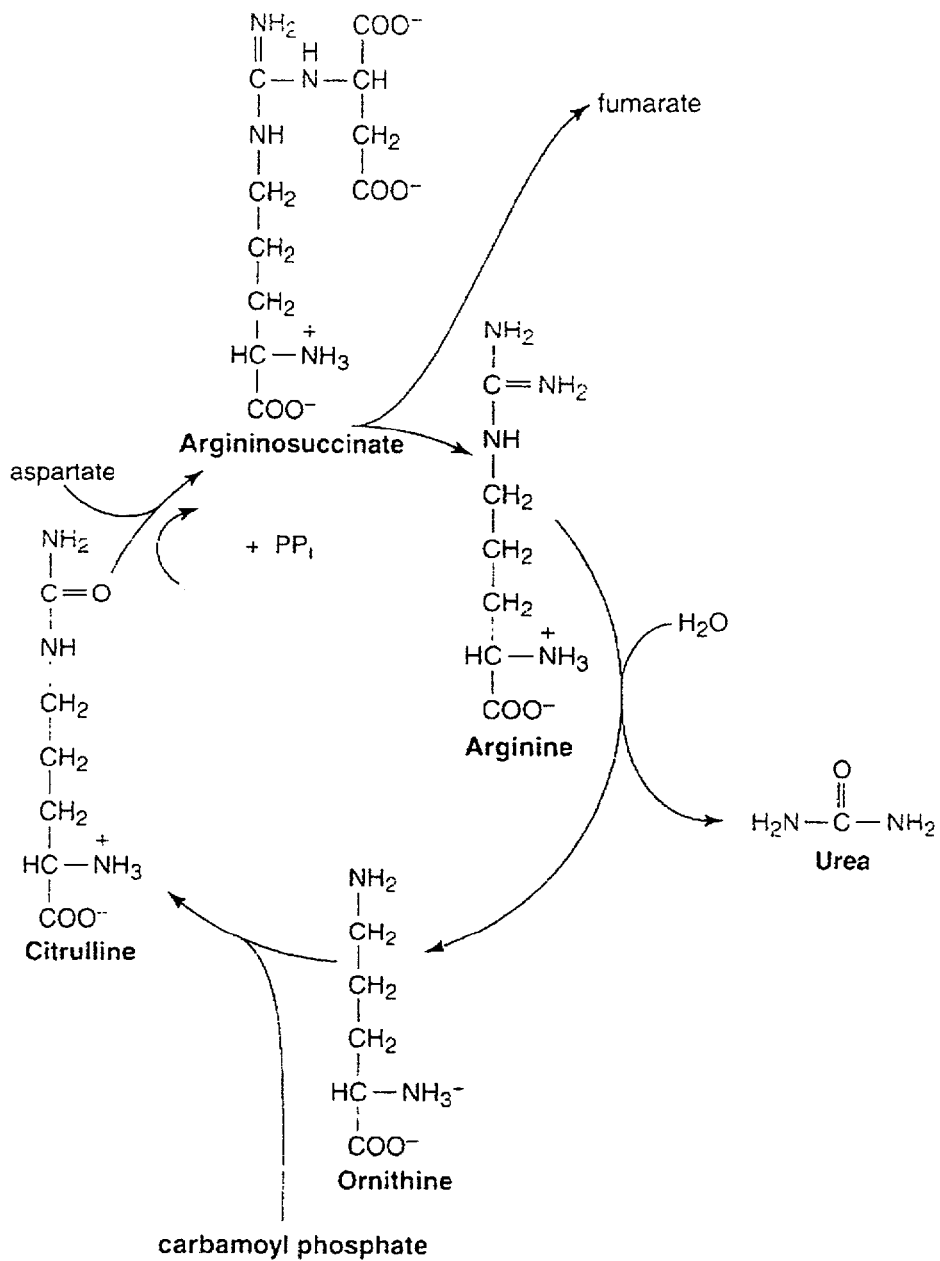

COMPOSITIONS OF BIOCHEMICAL COMPOUNDS INVOLVED IN BIOENERGY METABOLISM OF CELLS

CROSS-REFERENCE TO RELATED APPLICATION

This application claims the benefit under 35 U.S.C. § 1.119(e) of Provisional Application Ser. No. 60/268,825 filed Feb. 14, 2001, the disclosure of which is incorporated by reference in its entirety herein.

FIELD OF THE INVENTION

This invention relates to compositions of biochemical compounds involved in bioenergy metabolism of living cells and methods of use in the prevention and therapy of diseases in humans.

BACKGROUND OF THE INVENTION

The fact that many human diseases develop at the level of cells is well established. Rudolph Virchow's "Cellular Pathology" (Virchow Rudolph, *Cellular Pathology*, Berlin, 1858) has become a leading principle of pathology. While the localization of the initiation of these diseases—the cell—was thereby defined, the variety of mechanisms that cause a cell to malfunction have remained insufficiently understood.

One of these pathological mechanisms that have remained obscure is a deficiency or a lack of bioenergy in the cell. Under physiological conditions the bioenergy of a cell is provided from sugar, proteins and fats that is catabolyzed in the cell. The common pathways of catabolism of food and for the generation of bioenergy in form of ATP are the Tricarboxylic Acid Cycle or Citric Acid Cycle (Krebs cycle) and subsequent cellular energy pathway, the cellular Respiratory Chain (respiratory chain) as well as the closely connected Urea Cycle (urea cycle).

The possibility of a deficiency of one or more of the Krebs cycle, respiratory chain and the urea cycle compounds are further enhanced by the fact that these biochemical pathways involve a multitude of enzymatic steps. Just recently the first molecular diseases involving an enzyme deficiency of the Krebs cycle have been characterized (Bourgeron T., et al., *J. Clin. Invest.* 93:2514, 1994; Rustin et al., *Biochim Biophys Acta* 1361:185,1997; Patel, M. S. and Harris R. A. *FASEB J* 9:1164,1995; Shoffner, J. M. and Wallace D. C. in C. R. Scriver et al. (Eds.) *The Metabolic and Molecular Bases of Inherited Disease*, 7th ed. New York: McGraw-Hill, 1995, p. 1535). Genetic disorders for one or more of these enzymes and/or one or more of the coenzymes involved inevitably lead to a deficiency of one or more of the biochemical compounds of these pathways.

Recently, several coenzymes (e.g. thiamine, nicotinic acid, ascorbic acid, riboflavin, $Mg^{++}$) of the Krebs cycle have been used in the prevention and adjunct treatment of certain health conditions (Beyond deficiency, 2nd *Symposium of the New York Academy of Sciences on Vitamins*, New York 1992; E. Ziegler, L. J. Filer (eds.) *Present Knowledge in Nutrition* 7th edition. ILSI Press, Washington D.C. 1996; Matthias Rath, Alexandra Niedzwiecki. *J Appl. Nutrition* 48: 68–78, 1996). However, the biochemical compounds of the Krebs cycle itself, the respiratory chain and the closely connected urea cycle have not similarly been used.

Therefore there is a need for methods and compositions to prevent and treat malfunctioning of bioenergy metabolism of cells.

SUMMARY OF THE INVENTION

The present invention provides compositions of biochemical compounds involved in bioenergy metabolism of living cells.

The present invention provides a composition to improve bioenergy metabolism of cells comprising two or more chemical substances of Krebs cycle, wherein the chemical substances are intermediates of the cycle and/or precursors and cofactors thereof.

The present invention provides a composition to improve bioenergy metabolism of cells comprising two or more chemical substances of respiratory chain cycle, wherein the chemical substances are intermediates of the cycle and/or precursors and cofactors thereof.

The present invention provides a composition to improve bioenergy metabolism of cells comprising two or more chemical substances of urea cycle, wherein the chemical substances are intermediates of the cycle and/or precursors and cofactors.

The present invention provides methods of use of biochemical compounds involved in bioenergy metabolism of living cells in the prevention and therapy of diseases in humans.

The present invention provides a method for improving bioenergy metabolism of cells, comprising the step of administering to a human a composition which comprises two or more chemical substances of Krebs cycle, wherein the chemical substances are intermediates of the cycle and/or precursors and cofactors thereof.

The present invention provides a method for improving bioenergy metabolism of cells, comprising the step of administering to a human a composition which comprises two or more chemical substances of respiratory chain cycle, wherein the chemical substances are intermediates of the cycle and/or precursors and cofactors thereof.

The present invention provides a method for improving bioenergy metabolism of cells, comprising the step of administering to a human a composition which comprises two or more chemical substances of urea cycle, wherein the chemical substances are intermediates of the cycle and/or precursors and cofactors.

DESCRIPTION OF THE DRAWINGS

FIG. 1 depicts a graph showing the metabolic pathway of the Krebs cycle.

FIG. 2 depicts the enzyme complex and prosthetic group involved in the metabolic pathway of respiratory chain.

FIG. 3 depicts a graph showing the metabolic pathway of urea cycle.

DETAILED DESCRIPTION OF THE INVENTION

Life is not possible without sufficient bioenergy being created at the cellular level. In a series of metabolic pathway proteins, carbohydrates and fats are converted to adenosine triphosphate (ATP). Optimum availability of cellular energy is a precondition for health. Under normal conditions, e.g. in a young and healthy individual, the cells of the body create an optimum amount of cellular energy to maintain the diversified functions of the body.

With advanced age and under pathological conditions, the cells of the body are frequently not able to provide sufficient energy to maintain physiological functions of the body, despite optimum intake of food. Moreover, several inherited disorders have been identified in which enzymes of the cellular energy metabolism are affected, leading to neurological disorders and other clinical manifestations.

The common catabolism of food and the generation of bioenergy relate to the Krebs cycle, the cellular respiratory chain as well as the closely connected urea cycle. The basic biochemical compounds of the biochemical pathways have been elucidated. FIG. 1 summarizes the biochemical pathways of Krebs cycle. FIG. 2 summarizes the biochemical pathways of respiratory chain. FIG. 3 summarizes the biochemical pathways of urea cycle. While the biochemical structure of these compounds is known, they are currently not used in medicine as preventive and therapeutic agents.

a) The Krebs Cycle

The biochemical intermediates of the Krebs cycle claimed in this patent are: citrate, cis-aconitate, isocitrate, oxalsuccinate, α-Ketoglutarate, succinyl-coenzymA, succinate, fumarate, malate, oxalacetate as well as the biochemical compounds that are immediate precursors of the Krebs cycle, namely acetyl-coenzyme A and pyruvate.

Due to the varying importance of these compounds for energy metabolism, they were divided into two categories for the purposes of this invention:

A. Category A (Table 1): succinate, fumarate, L-malate, α-ketoglutarate.
B. Category B (Table 2): citrate, cis-aconitate, isocitrate, oxalsuccinate, succinyl-coenzyme A, oxalacetate as well as acetyl-coenzyme A and pyruvate.

Genetic defects affecting the Krebs cycle and other metabolic energy cycles of cells have been reported. Neuromuscular disorders may have underlying mitochondrial metabolic defects: reduction of mitochondrial malic enzyme activity (Stumpf et al. Friedreich attaxia: III. Mitochondrial Malic Enzym Deficiency, Neurology 1982; 32: 221–7). Fumarase deficiency patients have severe neurological impairment (e.g., progressive encephalopathy). Fumarase deficiency is an autosomal recessive enzephalopathy affecting both the mitochondrial and the cytosolic enzymes (Walker et al., *Journal of Inherited Metabolism Disorder* 12 (1989), 331–332; Gellera et al., *Neurology* 1990, 40 (3 Pt 1): 495–9; Bourgeron et al., *Journal of Clinical Investigations* 1994 June; 93 (6): 2514–8; Narajanan et al., *Journal of Children Neurologie* 1996 May; 11 (3): 252–55; Coughlin et al., *Mol. Genet. Meta.* 1998 April; 254–62).

Drugge et al. reported hereditary myopathy with legtic archdiocese, succinate dehydrogenase and aconitase deficiency (*J. Med. Genet.* 1995 May; 32 (5): 344–7). Dunkelman et al. reported 2 ketogluterate dehydrogenase deficiency with intermittents to ketoglutaric aceturia (*Neuropediatric* 2000 February; 31 (1): 35–8).). Thus, aconitase deficiency, 2-ketogluterate dehydrogenase deficiency and succinate dehydrogenase deficiency may be responsible for neurodegenerative diseases.

Current methodologies are lacking in finding means and methods to repair inherited and acquired mutations of genes encoding for enzymes essential for the compensation of deficiencies in the Krebs cycle and other metabolic energy cycles. Gene therapy remains widely theoretical. For example, repair of defective fumarase gene is still in experimental stage and it is still years from being applied in medicine. Moreover, gene therapy is associated with severe side-effects and high costs. There is so far no description of any composition of biochemical compounds nor their therapeutic use in the literature.

The present invention provides a method and composition for compensating such deficiencies in bioenergy metabolism by administering such lacking biochemical components to the body. The daily intake of the metabolic compounds of the Krebs cycle is further enhanced by the addition of ascorbate, thiamine, riboflavin, certain minerals and trace elements and other cofactors for the enzymatic reaction in this cycle. Optimum supply of these coenzymes can compensate—at least in part—for the insufficient availability of the enzyme itself due to a genetic defect, e.g., fumarase deficiency.

The present invention also provides the addition of NAD, NADH, FAD, FADH, NAPD, NAPD and other well known carrier of cellular energy has a synergistic effect to compensate for enzymatic defects of the Krebs cycle.

In a preferred embodiment, the present invention provides a composition comprising succinate, fumarate, L-malate, and α-ketoglutarate.

Preferably, the present invention relates to biochemical substances of the Krebs cycle are claimed as shown in Table 1, category A.

TABLE 1

| Krebs Cycle Compounds Category A | | |
|---|---|---|
| Biochemical Substances | Units | Amount claimed |
| Succinate | Mg | 0.01–100 |
| Fumarate | Mg | 0.01–100 |
| L-Malate | Mg | 0.01–100 |
| α-Ketoglutarate | Mg | 0.01–100 |

In another preferred embodiment, the present invention provides a composition comprising citrate, cis-aconitate, isocitrate, oxalsuccinate, succinyl-coenzyme A, oxalacetate as well as acetyl-coenzyme A and pyruvate.

Preferably, the present invention relates to biochemical substances of other intermediate steps of the Krebs cycle as shown in Table 2, category B.

TABLE 2

| Krebs Cycle Compounds Category B | | |
|---|---|---|
| Biochemical Substances | Units | Amount claimed |
| Pyruvate | Mg | 0.01–100 |
| Acetyl-Coenzyme A | Mg | 0.01–100 |
| Citrate | Mg | 0.01–200 |
| Cis-Aconitate | Mg | 0.01–100 |
| Isocitrate | Mg | 0.01–100 |
| Oxalsuccinate | Mg | 0.01–100 |
| 2-Oxo-Glutarate | Mg | 0.01–100 |
| Succinyl-CoenzymA | Mg | 0.01–100 |
| Oxaloacetate | Mg | 0.01–100 |

The bioenergy metabolic pathway, particularly the Krebs cycle, has been discovered a long time ago. Bioenergy metabolic pathway is very complex and is believed to take place in mostly closed systems. In skeletal muscle, the Krebs cycle functions as a closed cycle. It provides reducing equivalents to the electron-transport chain for ATP-synthesis and further provides essentially complete oxidation. In the liver, the Krebs cycle functions as an opened cycle. It allows carbon skeletons to enter and to leave the cycle at different sides and provides substrates for biosynthetic processes in the mitochondria and cytosol (Zinn et al., Fumerase Deficiency: The new cause of mitochondrial enzephallomyopathy, the New England Journal of Medicine, Volume 315, Aug. 21, 1986).

Although such deficiencies have been discovered many years ago, there seems to be a prejudice to administer compounds to compensate such deficiencies due to the described fact that such cycles are closed or allow only entrances of limited chemical compositions like carbon skeletons.

The present invention provides a specific composition of biochemical compounds that compensate enzyme deficiencies in the Krebs cycles in inherited or acquired defects. Without bound by any theory, the present invention discloses compositions of biochemical compounds that may compensate enzyme/intermediate deficiencies regardless whether Krebs cycle exists in closed or opened systems.

The present invention further provides compositions that have no known side effects and can be excreted from the bodies without any harm.

b) The Respiratory Chain

The biochemical compounds of the respiratory chain claimed are: coenzyme Q-10 (ubiquinone), ubihydroquinone(ubiquinol), other compounds of the ubiquinone/ubiquinol family of compounds, heme a (part of cytochrome a), heme b (part of cytochrome b) and heme c (part of cytochrome c).

Thus, deficiencies of the biochemical components of the respiratory chain may be a causative or contributing factor to the pathology of diseases.

The present invention provides a method and composition for compensating such deficiencies in respiratory chain metabolism by administering such lacking biochemical components to the body.

In a preferred embodiment, the present invention provides a composition comprising coenzyme Q-10 (ubiquinone), ubihydroquinone(ubiquinol), other compounds of the ubiquinone/ubiquinol family of compounds, heme a (part of cytochrome a), heme b (part of cytochrome b) and heme c (part of cytochrome c).

Preferably, the present invention relates to biochemical compounds of the Respiratory Chain (See Table 3) are claimed including coenzymes.

TABLE 3

Cellular Respiratory Chain Compounds

| Biochemical Substances | Units | Amount claimed |
| --- | --- | --- |
| Coenzyme Q-1O (Ubiquinone) | Mg | 0.01–20 |
| Ubihydroquinone (Ubiquinol) | Mg | 0.01–20 |
| Heme a (Part of Cytochrome a) | Mg | 0.01–20 |
| Heme b (Part of Cytochrome b) | Mg | 0.01–20 |
| Heme c (Part of Cytocbrome c) | Mg | 0.01–20 | c) The Urea Cycle

The biochemical compounds of the urea cycle are: citrulline, argininosuccinate, arginine, omithine and aspartate.

Thus, deficiencies of the biochemical components of the urea cycle may be a causative or contributing factor to the pathology of diseases.

The present invention provides a method and composition for compensating such deficiencies in urea cycle metabolism by administering such lacking biochemical components to the body.

In a preferred embodiment, the present invention provides a composition comprising citrulline, argininosuccinate, arginine, omithine and aspartate.

Preferably, the present invention provides biochemical compounds of the urea cycle (See Table 4).

TABLE 4

Cellular Urea Cycle Compounds

| Biochemical Substances | Units | Amount claimed |
| --- | --- | --- |
| Citrulline | Mg | 0.01–100 |
| Argininosuccinate | Mg | 0.01–100 |
| Arginine | Mg | 0.01–100 |
| Ornithine | Mg | 0.01–100 |
| Aspartate | Mg | 0.01–100 | d) The Cofactors of Cellular Energy Metabolism

The biochemical cofactors of cellular energy metabolism claimed include: lipoic acid, lipoamide, acetyl-lipoamide, lysine, carnitine, ascorbate, thiamine, riboflavin, nicotinic acid, niacinamide, pantothenate, nicotinamide-adenine dinucleotide (NAD), reduced nicotinamide adenine dinucleotide (NADH), nicotinamide-adenine dinucleotide phosphate (NADP), reduced NADP (NADPH), quinolinate (NAD/NADP precursor), flavin-adenine dinucleotide (FAD), reduced flavin-adenine dinucleotide (FADH), flavin mononucleotide (FMN), reduced flavin mononucleotide ($FMNH_2$), adenosine diphosphate (ADP), adenosine triphosphate (ATP), guanosine diphosphate (GDP), guanosine triphosphate (GTP), magnesium ($Mg^{++}$), calcium ($Ca^{++}$), manganese ($Mn^{++}$), copper iron-sulfate molybdenum.

Thus, deficiencies of the biochemical components of the cellular metabolism may be a causative or contributing factor to the pathology of diseases.

The present invention provides a method and composition for compensating such deficiencies in the cellular metabolism by administering such lacking biochemical components to the body.

In a preferred embodiment, the present invention provides a composition comprising lipoic acid, lipoamide, acetyl-lipoamide, lysine, carnitine, ascorbate, thiamine, riboflavin, nicotinic acid, niacinamide, pantothenate, nicotinamide-adenine dinucleotide (NAD), reduced nicotinamide adenine dinucleotide (NADH), nicotinamide-adenine dinucleotide phosphate (NADP), reduced NADP (NADPH), quinolinate (NAD/NADP precursor), flavin-adenine dinucleotide (FAD), reduced flavin-adenine dinucleotide (FADH), flavin mononucleotide (FMN), reduced flavin mononucleotide ($FMNH_2$), adenosine diphosphate (ADP), adenosine triphosphate (ATP), guanosine diphosphate (GDP), guanosine triphosphate (GTP), magnesium ($Mg^{++}$), calcium ($Ca^{++}$) manganese ($Mn^{++}$), copper iron-sulfate molybdenum.

Preferably, the present invention provides cofactors which enhance enzymatic reactions of metabolism and their precursors, vitamins and prosthetic groups and enzyme activators are claimed (See Table 5).

TABLE 5

Biochemical Cofactors of Cellular Energy Metabolism

| Biochemical Substances | Units | Amount claimed |
| --- | --- | --- |
| Lipoic Acid | mg | 0.01–100 |
| Lipoamide (Lipoic Acid + Lysine) | mg | 0.01–100 |
| Acetyl-Lipoamide | mg | 0.01–100 |
| Lysine | mg | 0.01–100 |
| Carnitine | mg | 0.01–100 |
| Ascorbate | mg | 0.01–200 |
| Thiamine | mg | 0.01–10 |
| Riboflavin | mg | 0.01–10 |

TABLE 5-continued

Biochemical Cofactors of Cellular Energy Metabolism

| Biochemical Substances | Units | Amount claimed |
|---|---|---|
| Nicotinic Acid | mg | 0.01–10 |
| Niacinamide | mg | 0.01–10 |
| Pantothenate | mg | 0.01–10 |
| Nicotinamide-Adenine Dinucleotide (NAD) | mg | 0.01–10 |
| Reduced Nicotinamide Adenine Dinucleotide (NADH) | mg | 0.01–10 |
| Nicotinamide-Adenine Dinucleotide Phosphate (NADP) | mg | 0.01–10 |
| Reduced NADP (NADPH) | mg | 0.01–10 |
| Quinolinate (NAD/NADP precursor) | mg | 0.01–10 |
| Flavin-Adenine Dinucleotide (FAD) | mg | 0.01–10 |
| Reduced Flavin-Adenine Dinucleotide (FADH) | mg | 0.01–10 |
| Flavin Mononucleotide (FMN) | mg | 0.01–10 |
| Reduced Flavin Mononucleotide ($FMNH_2$) | mg | 0.01–10 |
| Adenosine Diphosphate (ADP) | mg | 0.01–10 |
| Adenosine, Triphosphate (ATP) | mg | 0.01–10 |
| Guanosine Diphosphate (GDP) | mg | 0.01–10 |
| Guanosine Triphosphate (GTP) | mg | 0.01–10 |
| Magnesium ($Mg^{++}$) | mg | 0.01–10 |
| Calcium ($Ca^{++}$) | mg | 0.01–10 |
| Manganese ($Mn^{++}$) | mg | 0.01–10 |
| Copper | mg | 0.01–10 |
| Iron-Sulfate | mg | 0.01–10 |
| Molybdenum | mg | 0.01–10 | mg = milligrams

This invention provides the preventive and therapeutic use of biochemical intermediates of the Krebs cycle, and/or the respiration chain, the urea cycle alone or in combination with biochemical cofactors.

In a preferred embodiment, a composition of daily consumption of biochemical substances is listed in Table 6.

TABLE 6

Daily Composition of Biochemical Substances to Improve Bioenergy

| Biochemical Substances | Units | Amount per Day |
|---|---|---|
| Succinate | mg | 100 |
| Fumarate | mg | 100 |
| L-Malate | mg | 100 |
| α-Ketoglutarate | mg | 100 |
| Pyruvate | mg | 100 |
| Acetyl-CoA | mg | 100 |
| Citrate | mg | 200 |
| Cis-Aconitate | mg | 100 |
| Isocitrate | mg | 100 |
| Oxalsuccinate | mg | 100 |
| 2-Oxo-Glutarate | mg | 100 |
| Succinyl-Coenzyme A | mg | 100 |
| Coenzyme Q-10 (Ubiquinone) | mg | 20 |
| Ubihydroquinone (Ubiquinol) | mg | 20 |
| Arginine | mg | 100 |
| Carnitine | mg | 100 |
| Lysine | mg | 100 |
| Ascorbate | mg | 200 |
| Thiamine | mg | 10 |
| Riboflavin | mg | 10 |
| Nicotinic Acid | mg | 10 | mg = milligrams

The biochemical compounds disclosed in the present invention have broad application in medicine. The compounds claimed in this patent can be used in maintaining and restoring cellular energy to essentially every cell system in the body. Thus, the compounds claimed here can be used the prevention and therapy of a broad spectrum of diseases in humans as well as animals.

As for the application of these preventive and therapeutic steps, they are not limited to the prevention of neurological disorders or encephalopathy. A variety of other common diseases have been associated with deficiencies in cellular metabolism. Heart failure conditions, for example, affect close to 50 million people worldwide. The most common form, idiopathic cardiomyopathy, is caused by cellular malfunction of millions of cardiac myocytes. The most cause of this malfunction is an insufficient availability of cellular energy, depriving the myocytes of essential energy for the cardiac pumping function.

The present invention also provides compositions and methods for prevention and therapy of other health conditions. For example, the claimed invention may find therapeutic application in atherosclerosis, arteriosclerosis, occlusive cardiovascular, hypertension, diabetes and diabetic complications, arrhythmia, irregular heart beat, lipid and lipoprotein disorders, hypercholesterolemia, hypertriglyceridemia, hyperlipoprotein(a), homocysteinuria, neoplastic diseases, storage diseases and other inherited metabolic disorders, Down Syndrome and other inherited disorders, inflammatory diseases, arthritis, skin disorders, neurodermatitis, allergic conditions, allergic and non-allergic asthma, neurological disorders, Parkinson's Disease, Alzheimer's Disease, dementia, multiple sclerosis, migraines, premature aging, degenerative diseases, osteoporosis, infectious diseases, and autoimmune disorders.

The present invention provides compositions of biochemical compounds of the biochemical pathways and restores essential bioenergy molecules that would maintain an optimum level of cellular energy metabolism in the cells and thereby contribute to the prevention and therapy of organ malfunction and diseases.

The present invention further provides compositions of biochemical substances involved in the bioenergy metabolism of cells, particularly in the Krebs cycle, the respiratory chain and the urea cycle. This comprises intermediates of such cycles and precursors and cofactors thereof.

The details of one or more embodiments of the invention are set forth in the accompanying drawings and the description below. Other features, objects, and advantages of the invention will be apparent from the description and drawings, and from the claims. All the references cited are hereby incorporated by reference in their entireties. It is understood that various modifications may be made without departing from the spirit and scope of the invention.

What is claimed is:

1. A composition for improving bioenergy metabolism of cells, wherein the composition consists of a pharmaceutically acceptable carrier; and

| Biochemical Substances | Amount |
|---|---|
| Succinate | 0.01–100 mg; |
| Fumarate | 0.01–100 mg; |
| L-Malate | 0.01–100 mg; and |
| α-Ketoglutarate | 0.01–100 mg. |

2. A composition for improving bioenergy metabolism of cells, wherein the composition consists of a pharmaceutically acceptable carrier; and

| Biochemical Substances | Amount |
|---|---|
| Pyruvate | 0.01–100 mg; |
| Acetyl-Coenzyme A | 0.01–100 mg; |
| Citrate | 0.01–200 mg; |
| Cis-Aconitate | 0.01–100 mg; |
| Isocitrate | 0.01–100 mg; |
| Oxalsuccinate | 0.01–100 mg; |
| 2-Oxo-Glutarate | 0.01–100 mg; |
| Succinyl-CoenzymA | 0.01–100 mg; and |
| Oxaloacetate | 0.01–100 mg. |

3. A composition for improving bioenergy metabolism of cells, wherein the composition consists of a pharmaceutically acceptable carrier; and

| Biochemical Substances | Amount |
|---|---|
| Lipoic Acid | 0.01–100 mg; |
| Lipoamide (Lipoic Acid + Lysine); | 0.01–100 mg |
| Acetyl-Lipoamide | 0.01–100 mg; |
| Lysine | 0.01–100 mg; |
| Carnitine | 0.01–100 mg; |
| Ascorbate | 0.01–200 mg; |
| Thiamine | 0.01–10 mg; |
| Riboflavin | 0.01–10 mg; |
| Nicotinic Acid | 0.01–10 mg; |
| Niacinamide | 0.01–10 mg; |
| Pantothenate | 0.01–10 mg; |
| Nicotinamide-Adenine Dinucleotide (NAD) | 0.01–10 mg; |
| Reduced Nicotinamide Adenine Dinucleotide (NADH) | 0.01–10 mg; |
| Nicotinamide-Adenine Dinucleotide Phosphate (NADP) reduced NADP (NADPH) | 0.01–10 mg; |
| Quinolinate (NAD/NADP precursor) | 0.01–10 mg; |
| Flavin-Adenine Dinucleotide (FAD) | 0.01–10 mg; |
| Reduced Flavin-Adenine Dinucleotide (FADH) | 0.01–10 mg; |
| Flavin Mononucleotide (FMN) | 0.01–10 mg; |
| Reduced Flavin Mononucleotide (FMNH$_2$) | 0.01–10 mg; |
| Adenosine Diphosphate (ADP) | 0.01–10 mg; |
| Adenosine, Triphosphate (ATP) | 0.01–10 mg; |
| Guanosine Diphosphate (GDP) | 0.01–10 mg; |
| Guanosine Triphosphate (GTP) | 0.01–10 mg; |
| Magnesium (Mg$^{++}$) | 0.01–10 mg; |
| Calcium (Ca$^{2+}$) | 0.01–10 mg; |
| Manganese (Mn$^{2+}$) | 0.01–10 mg; |
| Copper | 0.01–10 mg; |
| Iron-Sulfate | 0.01–10 mg; and |
| Molybdenum | 0.01–10 mg. |

* * * * *